United States Patent [19]

Kessel

[11] 4,054,131

[45] Oct. 18, 1977

[54] INTRAUTERINE CONTRACEPTIVE DEVICE

[75] Inventor: Elton Kessel, Chapel Hill, N.C.

[73] Assignee: International Pregnancy Advisory Services, Chapel Hill, N.C.

[21] Appl. No.: 713,233

[22] Filed: Aug. 10, 1976

[51] Int. Cl.² ............................................. A61F 5/46
[52] U.S. Cl. ...................................................... 128/130
[58] Field of Search ........................ 128/130, 260, 127

[56] References Cited

U.S. PATENT DOCUMENTS

| | | | |
|---|---|---|---|
| 3,511,231 | 5/1970 | Robinson | 128/130 |
| 3,898,986 | 8/1975 | Zaffaroni | 128/130 |
| 3,913,573 | 10/1975 | Gutnick | 128/130 |
| 3,937,217 | 2/1976 | Kosonen | 128/130 |
| 3,952,734 | 4/1976 | Os et al. | 128/130 |
| 3,993,057 | 11/1976 | Ramwell | 128/130 |

Primary Examiner—Lawrence W. Trapp
Attorney, Agent, or Firm—B. B. Olive

[57] ABSTRACT

An integral intrauterine contraceptive device comprises a relatively thick elongated stem, a downwardly bowed crossbar secured to the top of the stem, and a pair of downwardly and inwardly extending arms formed as continuations of the crossbar. The crossbar and arm construction is designed for atraumatic embedding in the endometrium to reduce expulsion caused by uterine contractions.

14 Claims, 11 Drawing Figures

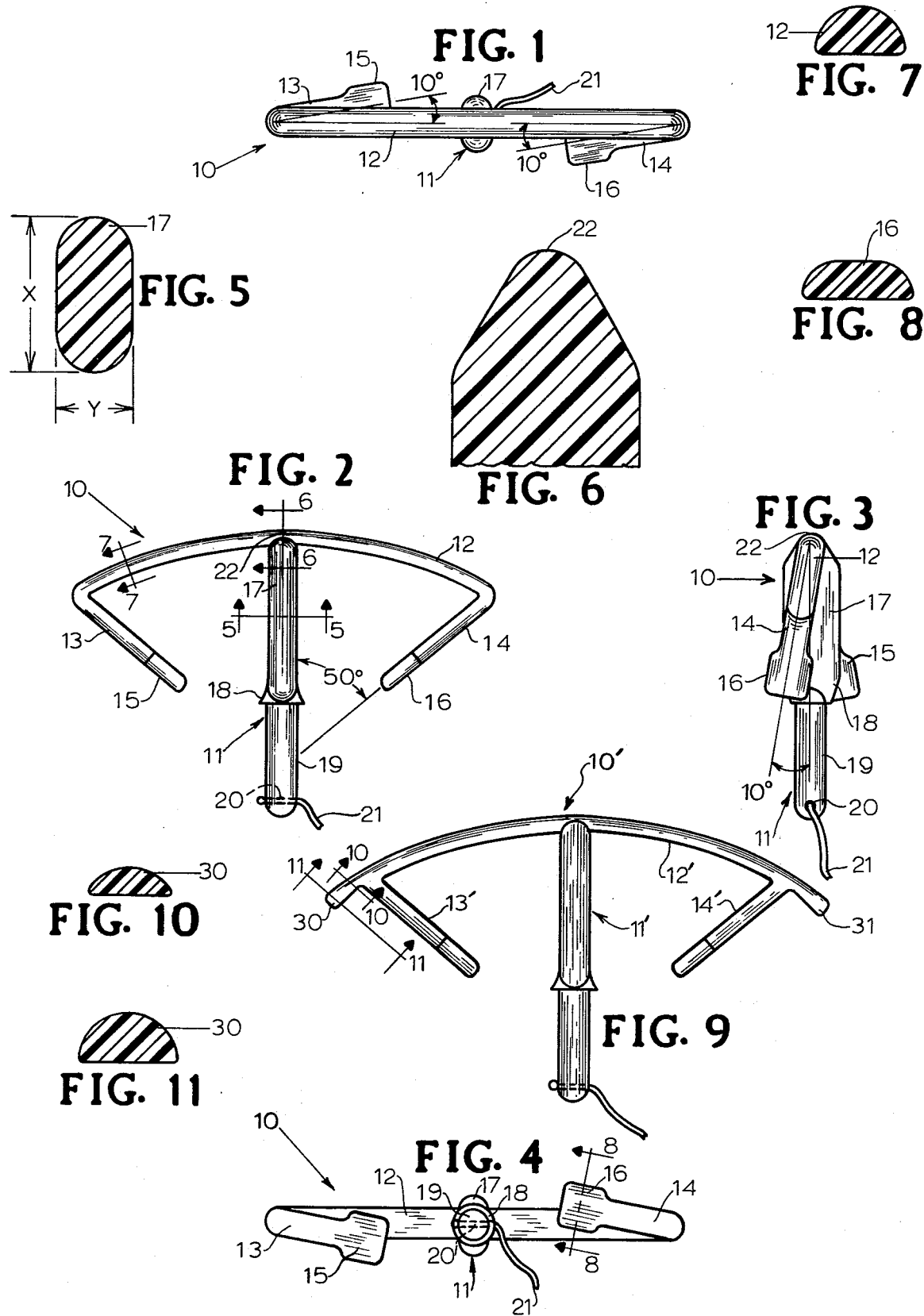

INTRAUTERINE CONTRACEPTIVE DEVICE

BACKGROUND OF THE INVENTION

1. Field of the Invention

This invention relates to contraceptive devices and particularly to intrauterine contraceptive devices.

2. Description of the Prior Art

U.S. Pat. No. 3,533,406 discloses an intrauterine contraceptive device having a "T" shape. The device is completely placed into the endometrial cavity where the end of the stem extends toward the cervical os when the crossbar of the "T" lies at the fundus of the uterus. The contraceptive efficacy of the "T" device has proven unacceptable for many families. As a result, the "T" device has been used in many applications as a carrier for contraceptive chemicals such as copper. It is believed that the relatively small cross section of the stem of the "T" device prevents it from having the desired contraceptive effect. The so-called "7" shaped devices have produced effects nearly identical to the "T" devices. Both the "T" and "7" devices are lightweight and embed somewhat in the endometrial tissue. Expulsion rates and bleeding are modest, primarily because of the form and size of the devices.

U.S. Pat. No. 3,881,475 discloses an intrauterine contraceptive device having a pair of loops extending in opposite directions from a common stem. Each loop has a free end. This design has attempted to provide a device wherein the loops are capable of more readily conforming to the walls of the uterine cavity and are soft enough to move with the uterine walls as they move or contract. Higher expulsion rates and removal rates are reported with use of the device.

U.S. Pat. No. 3,937,217 provides an intrauterine contraceptive device which resembles the "T" device but which has a loop formed in the end of the stem and has a less rigid crossbar construction. This patented device has as its primary object the reduction of bleeding, involuntary expulsion and occasional perforation into the cervix associated with the "T" device. Other intrauterine contraceptive devices having similar constructions are described in U.S. Pats. Nos. 3,454,004; 3,457,915; 3,810,456 and 3,842,826.

Thus, it becomes an object of the present invention to provide an intrauterine contraceptive device having the advantages associated with the above-described devices, but with increased contraceptive efficacy, lower expulsion rates and less bleeding and pain for the patient.

SUMMARY OF THE INVENTION

The present invention provides an intrauterine contraceptive device having a relatively thick stem, a downwardly bowed crossbar secured to the top of the stem and a pair of downwardly and inwardly extending arms formed as continuations of the cross bar with the free ends of the arms terminating as enlarged fin-like portions. The crossbar and stem are adapted to lie in the fold between the anterior and posterior walls of the endometrium with the upper portion of the stem being of a round-ended rectangular, elliptical-like cross section with the plane of the long axis thereof being perpendicular to the crossbar and providing a stem thickness of 4mm to 6mm between such walls. The shape and resilience of the crossbar and arms serve to propel the device toward the fundus during uterine contractions thereby reducing the chance of expulsion. The simple design makes possible a lighweight device which results in reduced bleeding and pain for the patient. The mentioned 4mm to 6mm dimension represents a preferred thickness for the desired results.

DESCRIPTION OF THE DRAWINGS

FIG. 1 is a top plan view of the intrauterine contraceptive device of the present invention.

FIG. 2 is a side elevation view of the device.

FIG. 3 is an end elevation view of the device.

FIG. 4 is a bottom plan view of the device.

FIG. 5 is an enlarged section view taken substantially along line 5—5 of FIG. 2.

FIG. 6 is an enlarged, fragmentary section view taken substantially along line 6—6 of FIG. 2.

FIG. 7 is an enlarged section view taken substantially along line 7—7 of FIG. 2.

FIG. 8 is an enlarged section view taken substantially along line 8—8 of FIG. 4.

FIG. 9 is a side elevation view of an alternative embodiment of the invention device.

FIG. 10 is an enlarged section view taken substantially along line 10—10 of FIG. 9.

FIG. 11 is an enlarged section view taken substantially along line 11—11 of FIG. 9.

DESCRIPTION OF THE PREFERRED EMBODIMENT

Referring to the drawings, the intrauterine contraceptive device 10 of the present invention includes a relatively thick stem 11, a downwardly bowed crossbar 12 and a pair of inwardly extending arms 13, 14 formed as continuations of crossbar 12. Stem 11 is formed with an upper portion 17 which is somewhat elliptical or of round-ended rectangular shape in cross section. In the specific embodiment, the major or long axis X (FIG. 5) of this section of approximately 4mm with the minor axis Y (FIG. 5) being approximately 2mm. A continuous circular lip 18 is formed at the base of upper portion 17 to act as an abutment for an inserter tube (not shown). The lower end 19 of stem 11 is circular in cross section and is smaller in cross sectional area than that of upper portion 17. Dimension X provides a desired thickness.

A pair of arms 13, 14 are formed as continuations of crossbar 12 and project downwardly and inwardly toward stem 11 and terminate short of touching the stem. The line of each of the arms 13, 14 defines an included angle of 50° with respect to the central axis of the stem, with 40° to 70° being an acceptable range (see FIG. 2). Also, arms 13, 14 are angled 10° in opposite directions out of the central plane through the stem and cross bar (see FIGS. 1, 3 and 4) to allow the arms to cross over and slide by the lower end 19 of stem 11 during insertion.

For insertion, the lower end 19 of stem 11 slidably fits into the end of an inserter tube. The curved leading portion 22 of device 10 is then inserted into the uterus, at which time crossbar 12 becomes bowed further downwardly and arms 13, 14 cross over stem 11. The device is fully inserted when the cross bar lies adjacent the fundus of the uterus. It should be noted that the device may be constructed with the arms 13, 14 in the same plane with stem 11 and crossbar 12 (i.e., without the above-described 10° offsets). However, with such an alternative construction, the arms 13, 14 do not automatically cross over stem 11 and the inserter tube during insertion unless the physician first rotates the arms out of the mentioned plane so that they will assume a momentary "fix" in an offset position and will retain such fix during insertion. This alternative construction has proven adequate but it does require an added step to be performed by the physician.

The leading portion 22 of the device is tapered, as seen in FIG. 6, to gently dilate the internal os during insertion. Once the device 10 is fully inserted, crossbar 12 and arms 13, 14 return to their normal positions. A small hole 20 in end 19 receives a withdrawal thread 21 useful for removal of the device in the manner well known to those skilled in the art.

As illustrated in FIGS. 7 and 8, crossbar 12 and arms 13, 14 have half-round cross sections which provide atraumatic embedding in the anterior and posterior walls of the endometrium. The unique shape of device 10 allows the device to resist expulsion due to contractions of the uterus and thereby maintain a position at the fundus. Contractions of the fundus of the uterus cause crossbar 12 to bow further and propel the device further towards the fundus. Contractions of the lower uterine segment impinge on arms 13, 14 and also serve to propel the device toward the fundus. A pair of flat fins 15, 16 are formed at the tips of arms 13, 14 to reduce the possibility of the arms perforating the tissue during contractions of the uterus or during insertion and orient as shown.

The contraceptive efficacy of the device may be primarily attributed to the thickness (approximately 5mm) of the upper portion 17 of stem 11 as seen in cross section in FIG. 5. A thickness of 5mm is preferred, with 4.0 to 6.0mm being an acceptable range. Although device 10 has a greater thickness at the critical point (i.e., upper stem portion 17), the overall mass of the device is substantially less than most contraceptive devices. This reduced mass is the primary reason for the low levels of bleeding and pain associated with the device and the reduced tendency of the uterus to expel the device.

In the illustrated embodiment, shaft 11 has a length of approximately 20mm with end 19 being 8mm in length and upper portion 17 being 12mm. End 19 has an outside diameter of approximately 2mm, which corresponds with the inside diameter of the inserted tube (not shown). Crossbar 12 spans 30mm (approximately the lateral dimension of the fundus) and has a radius of curvature on the order of 30mm. Crossbar 12 and arms 13, 14 are half-round in cross section with an outward curved surface and an inward flat surface which has a width of approximately 2mm. Fins 15, 16 flatten out to approximately 3mm in width. Since the entire device 10 is not placed within an inserter tube, the device does not have to have a fully resilient "memory" for returning to its normal shape after substantial periods of distortion. As explained above, during insertion only the crossbar 12 and arms 13, 14 are distorted. These members easily return to their normal positions when the device 10 is fully inserted and comes to rest between the anterior and posterior walls of the endometrium.

Referring now to FIGS. 9, 10 and 11, an alternative embodiment intrauterine contraceptive device 10' is illustrated as having a pair of crossbar extensions 30, 31 which extend beyond the intersection point of arms 13', 14'. Extensions 30, 31 provide further atraumatic embedding in the walls of the endometrium. Extensions 30, 31 further resist expulsion due to contractions of the uterus and thereby maintains device 10' in position at the fundus. Thus, where additional atraumatic embedding and expulsion resistance is desired this alternative embodiment may be employed.

From the foregoing description, it may be seen that the art is now provided with an intrauterine contraceptive device having (1) an improved contraceptive efficacy due in large part to the stem thickness which is disposed between the anterior and posterior walls of the endometrium; (2) a very low expulsion rate deriving from the atraumatic embedding of the crossbar and arms in the endometrium and the tendency of the crossbar and arms to propel the device toward the fundus during uterine contractions; (3) a reduced tendency to cause bleeding and pain due to its low mass; and (4) a resilient construction allowing ease of insertion without the physician having to insert the entire device into an inserter tube. Those skilled in the art will recognize that the present invention represents a substantial departure from the prior art and that the invention is not limited solely to the specific embodiment described in detail.

The plastic material used to mold the described device as an integral structure may be polyethelene, an ethylene-vinyl acetate (EVA) copolymer or any like material well known in the art.

What is claimed is:

1. An intrauterine contraceptive device comprising:
   a. an elongated stem having an upper portion and a lower portion;
   b. a resilient downwardly bowed crossbar integrally secured at its midpoint to the tip of said stem upper portion; and
   c. a pair of resilient arms formed as integral continuations of the opposed ends of said crossbar, said arms being angled downwardly and inwardly toward said stem and terminating short of touching said stem, and the line of each of said arms defining an included angle with the central axis of said stem of between 40° and 70°.

2. A device as claimed in claim 1 wherein said stem upper end has a thickness of between 4.0 to 6.0mm as measured in a plane perpendicular to said crossbar to provide such thickness in a plane perpendicular to the anterior and posterior walls of the endometrium when the device is inserted in the uterus.

3. A device as claimed in claim 2 wherein said thickness is 4mm.

4. A device as claimed in claim 1 wherein said included angle is on the order of 50°.

5. A device as claimed in claim 1 wherein said arms include flat fin portions at their ends oriented to reduce tissue penetration of said arms during use of said device.

6. A device as claimed in claim 1 wherein said arms are angled in opposite directions out of the central plane through the stem and crossbar adapting said arms to cross over and slide by said stem during insertion of the device.

7. A device as claimed in claim 6 wherein each said arm is angled out of said plane by an angle on the order of 10°.

8. A device as claimed in claim 7 including a pair of crossbar extensions forming a continuation of said crossbar beyond the point of intersection of said arms and said crossbar and adapted to provide additional embedding of said device during use thereof.

9. A device as claimed in claim 1 wherein said stem is on the order of 20mm in length and said crossbar spans a distance on the order of 30mm and has a radius of curvature on the order of 30mm.

10. An intrauterine contraceptive device adapted to lie in the fold between the anterior and posterior walls of the endometrium comprising:
- a. an elongated stem having a lower portion and an upper portion, said upper portion having a thickness between 4.0 to 6.0mm in a direction perpendicular to the anterior and posterior walls of the endometrium with said device installed therebetween and said lower portion having an outside diameter adapted for being slidably received by an inserter tube;
- b. a resilient downwardly bowed crossbar integrally secured at its midpoint to the tip of said stem upper portion; and
- c. a pair of resilient arms formed as integral continuations of the opposed ends of said crossbar, said arms being angled downwardly and inwardly toward said stem and terminating short of touching said stem, and the line of each of said arms defining an included angle with the central axis of said stem of between 40° and 70°, said arms having flat fin-like portions at the ends thereof oriented to reduce tissue penetration during use thereof, and said arms being angled in opposite directions out of the central plane through the stem and crossbar.

11. A device as claimed in claim 10 wherein said upper stem portion thickness is 4mm.

12. A device as claimed in claim 11 wherein said included angle is on the order of 50°.

13. A device as claimed in claim 12 wherein each said arm is angled out of said plane by an angle on the order of 10°.

14. A device as claimed in claim 13 wherein said stem is on the order of 20mm in length and said crossbar spans a distance on the order of 30mm and has a radius of curvature on the order of 30mm.

* * * * *